(12) United States Patent
Zino Gutierrez

(10) Patent No.: US 8,337,473 B2
(45) Date of Patent: Dec. 25, 2012

(54) SUBSTANCE DISPENSER, ESPECIALLY FOR MEDICAL OR COSMETIC TREATMENT

(76) Inventor: Christian Javier Zino Gutierrez, Buenos Aires (AR)

( * ) Notice: Subject to any disclaimer, the term of this patent is extended or adjusted under 35 U.S.C. 154(b) by 285 days.

(21) Appl. No.: 12/838,379

(22) Filed: Jul. 16, 2010

(65) Prior Publication Data

US 2012/0016319 A1    Jan. 19, 2012

(51) Int. Cl.
*A61M 35/00* (2006.01)
*B05C 17/01* (2006.01)
(52) U.S. Cl. .................. 604/311; 401/150; 604/289
(58) Field of Classification Search .......... 604/310–311, 604/290; 40/150, 178
See application file for complete search history.

(56) References Cited

U.S. PATENT DOCUMENTS

| | | | | |
|---|---|---|---|---|
| 52,928 A * | 2/1866 | Fogerty | .......................... | 100/213 |
| 543,200 A * | 7/1895 | Verpillier | ...................... | 401/172 |
| 767,469 A * | 8/1904 | Ziegler | .......................... | 401/176 |
| 850,357 A * | 4/1907 | Doyle | ............................ | 604/311 |
| 1,839,742 A * | 1/1932 | Davis | .............................. | 401/28 |
| 1,857,857 A * | 5/1932 | Medley | ......................... | 401/176 |
| 1,988,088 A * | 1/1935 | Philippe | ....................... | 401/172 |
| 2,085,446 A * | 6/1937 | Philippe | ....................... | 222/386 |
| 2,431,985 A * | 12/1947 | Bowman et al. | ................ | 604/47 |
| 2,616,423 A * | 11/1952 | Kurkjian | ....................... | 604/200 |
| 2,847,009 A * | 8/1958 | Blease | ........................... | 604/227 |
| 2,860,635 A * | 11/1958 | Wilburn | ........................ | 604/190 |
| 2,917,765 A * | 12/1959 | Jakubowski | ................... | 401/175 |
| 3,010,138 A * | 11/1961 | Nadai | .............................. | 401/13 |
| 3,493,503 A * | 2/1970 | Morris | .......................... | 210/778 |
| 3,519,364 A * | 7/1970 | Andrew | ......................... | 401/177 |
| 3,650,093 A * | 3/1972 | Rosenberg | .......................... | 96/6 |
| 3,874,851 A * | 4/1975 | Wilkins et al. | ................... | 435/30 |
| 3,903,888 A * | 9/1975 | Buelow et al. | ................ | 604/186 |
| 3,933,652 A * | 1/1976 | Weichselbaum et al. | ..... | 210/446 |
| 4,121,525 A * | 10/1978 | Courtis | .......................... | 111/200 |
| 4,415,288 A * | 11/1983 | Gordon et al. | ................ | 401/132 |
| 4,498,796 A * | 2/1985 | Gordon et al. | ................ | 401/132 |
| 4,578,055 A * | 3/1986 | Fischer | .............................. | 604/2 |
| 4,596,561 A * | 6/1986 | Meyer et al. | ................... | 604/190 |
| 4,974,756 A * | 12/1990 | Pearson et al. | ................ | 222/562 |
| 4,997,371 A * | 3/1991 | Fischer | .......................... | 433/90 |
| 5,246,371 A * | 9/1993 | Fischer | ...................... | 433/217.1 |
| 5,269,684 A * | 12/1993 | Fischer | .......................... | 433/90 |
| 5,286,257 A * | 2/1994 | Fischer | .......................... | 604/82 |
| 5,413,253 A * | 5/1995 | Simmen | ......................... | 222/137 |
| 5,453,093 A * | 9/1995 | Haining | ......................... | 604/110 |
| 5,489,280 A * | 2/1996 | Russell | .......................... | 604/311 |
| 5,609,271 A * | 3/1997 | Keller et al. | ................ | 222/145.6 |
| 5,615,962 A * | 4/1997 | Staub | .............................. | 401/173 |
| 5,816,804 A * | 10/1998 | Fischer | .......................... | 433/90 |
| 5,819,988 A * | 10/1998 | Sawhney et al. | ............... | 222/137 |
| 5,833,382 A * | 11/1998 | Jenks et al. | ..................... | 401/82 |
| 6,009,887 A * | 1/2000 | Hertel | ........................... | 132/317 |
| 6,045,279 A * | 4/2000 | Follis | ................................ | 401/6 |

(Continued)

*Primary Examiner* — Melanie Hand
*Assistant Examiner* — Paula Craig
(74) *Attorney, Agent, or Firm* — Steinfl & Bruno LLP

(57) ABSTRACT

A dispenser containing a substance to be applied on a patient is described. The dispenser includes a plunger, a tube and a perforated element located inside the tube. The tube contains openings at its application end. When the plunger is pushed during application, the substance is squeezed through the perforated element and the openings and is applied to the patient. Selection of the height of the perforated element and presence or absence of alignment between the perforations of the perforated element and the openings allows control of the application of the substance on the patient.

14 Claims, 6 Drawing Sheets

U.S. PATENT DOCUMENTS

| | | | |
|---|---|---|---|
| 6,065,645 A * | 5/2000 | Sawhney et al. | 222/137 |
| 6,129,894 A * | 10/2000 | Rabenecker et al. | 422/430 |
| 6,190,367 B1 * | 2/2001 | Hall | 604/290 |
| 6,210,057 B1 * | 4/2001 | Yannaci et al. | 401/6 |
| 8,029,204 B2 * | 10/2011 | DeVirag et al. | 401/75 |
| 2006/0039742 A1 * | 2/2006 | Cable et al. | 401/134 |
| 2009/0152300 A1 * | 6/2009 | Hayman et al. | 222/145.6 |
| 2009/0270814 A1 * | 10/2009 | Masi et al. | 604/190 |
| 2009/0281504 A1 * | 11/2009 | Nanba et al. | 604/190 |
| 2010/0160873 A1 * | 6/2010 | Goldrain | 604/311 |

* cited by examiner

SUBSTANCE DISPENSER, ESPECIALLY FOR MEDICAL OR COSMETIC TREATMENT

FIELD

The present disclosure is directed to a substance dispenser, especially for medical or cosmetic treatment, for dispensing substances such as gels, creams, pastes, glue and similar. Such substances are to be dispensed on the human or animal skin and can have a medical or a non-medical (e.g., cosmetic, beauty, etc) application.

BACKGROUND

Most substances used in the beauty and/or health fields to be applied to a human or animal patient are spread on the skin of the patient through the hands of an operator (e.g., a nurse), by covering such hands with medical gloves. Another example is the use of recipients to contain the substance and spatulas to spread the substance on the patient. In both cases, such substances come easily in contact with air, thus increasing their chance of being contaminated and/or deteriorated in view of the room temperature.

SUMMARY

According to an aspect of the disclosure, a dispenser adapted to contain a substance to be applied on a human or animal patient is provided, comprising: a plunger; a tube, the plunger being adapted to slide inside the tube for application of the substance, the tube containing one or more openings at a first end region thereof, the first end region adapted to be located in proximity of or on a body region of the human or animal patient; a perforated element located inside the tube, wherein location of the perforated element inside the tube is such that the substance to be applied is adapted to be disposed inside the tube above the perforated element before application, and wherein, during use of the dispenser, the plunger slides inside the tube to push the substance through the perforated element and the one or more openings at the first end region of the tube, thus expelling the substance from the dispenser for application on the human or animal patient.

According to a further aspect, a dispenser adapted to contain a substance is provided, comprising: a plunger; a tube, the plunger being adapted to slide inside the tube for application of the substance, the tube containing one or more openings at a first end region thereof; a perforated element located inside the tube, wherein location of the perforated element inside the tube is such that the substance to be applied is adapted to be disposed inside the tube above the perforated element before application, and wherein, during use of the dispenser, the plunger slides inside the tube to push the substance through the perforated element and the one or more openings at the first end region of the tube, thus expelling the substance from the dispenser.

As the dispenser can be disposable after use, any kind of pathogens, bacteria, fungi, parasites that may have contacted the dispenser from the body of a patient, will not be transmitted to the next patient.

Additionally, the dispenser allows a controlled distribution of the amount of substance in accordance with the various uses and applications.

The substances can be prefilled in the dispenser, e.g. upon fabrication, or can be inserted in the dispenser right before application.

Further uses of the dispenser can be non-medical or non-cosmetic uses, such as application of a glue through the dispenser, application of a sauce through the dispenser, and so on.

BRIEF DESCRIPTION OF THE DRAWINGS

Reference will now be made to the enclosed figures, which are provided herewith by way of example and not of limitation. In particular.

DESCRIPTION

Figure 1:
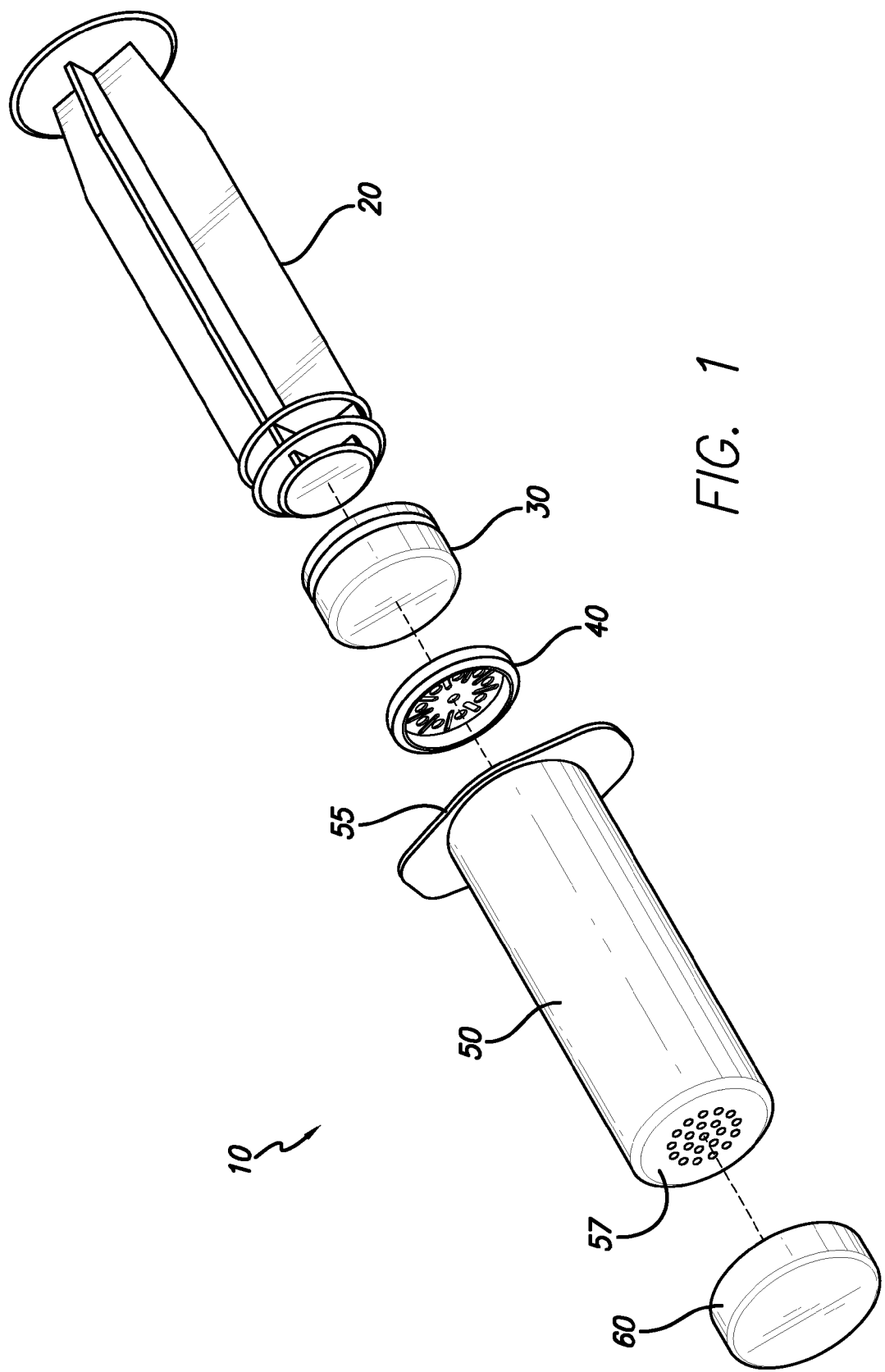
FIG. 1 shows a perspective exploded view of an embodiment of the dispenser according to the present disclosure.
Figure 2:
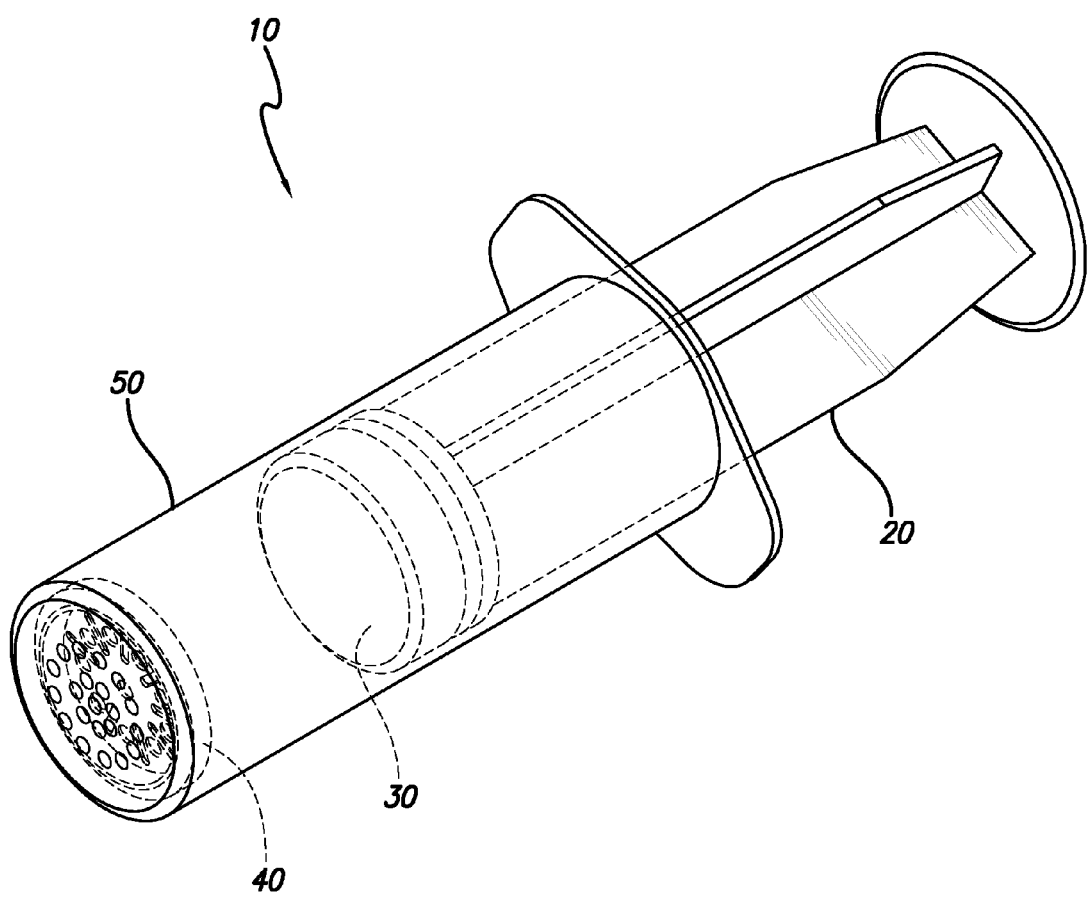
FIG. 2 shows a perspective view of the dispenser showing movement of a dispenser's plunger inside a tube towards a perforated element.

FIG. 1 shows a perspective exploded view of an embodiment of the dispenser according to the present disclosure. The dispenser (10) comprises a rod or plunger (20) inclusive of a plunger end or plunger ring (30). During use of the dispenser (10), the plunger ring (30) is adapted to come into contact with a perforated element (40) which is shown between the plunger ring (30) and a tube (50) in the exploded view of FIG. 1, but which is located inside the tube (50) at its bottom during operation, as better shown in the perspective view of FIG. 2, where movement of the plunger (20) towards the bottom of the tube (50) and hence towards the perforated element (40) is shown. Turning back to FIG. 1, tube (50) is open at its upper end (55) and exhibits a perforated bottom (57), as later discussed. Also shown in FIG. 1 is a cap (60), adapted to close the perforated bottom (57) of the tube (50) when the dispenser (10) is not in use.

Figure 3:
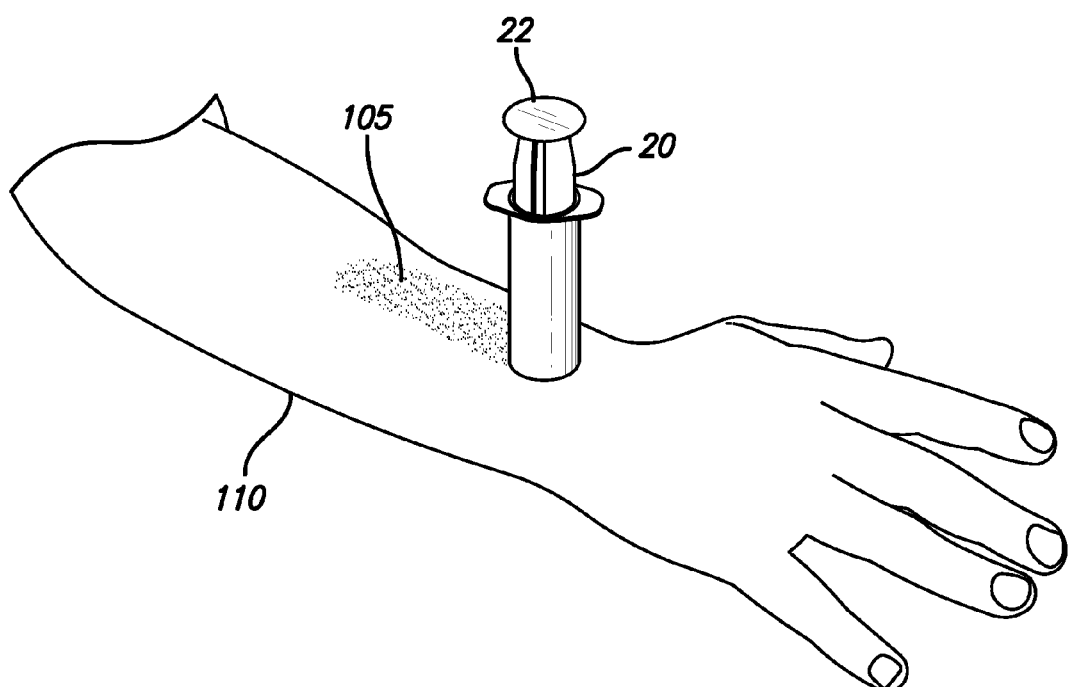
FIG. 3 shows an exemplary use of the dispenser on the skin of a patient.

The substance (e.g., gel) to be used and to be applied on the skin of a patient through the dispenser (10) is located in the tube (50) above the perforated element (40). During use, the cap (60) is removed and the perforated bottom (57) of the tube (50) is placed in proximity of the patient's skin, as shown in FIG. 3. The operator (not shown) pushes the plunger (20) along its upper end (22) with a thumb towards the inside of the tube (50), thus allowing the plunger (20) to slide inside the tube (50) and at the same time compressing the substance inside the tube (50). Compression of the substance forces the substance to pass through the openings (42, 43) in the perforated element (40) (see also FIGS. 4 and 5) and the openings (58) of the perforated bottom (57) of the tube (50), thus reaching the skin of the patient, as shown in FIG. 3, where application of the substance (105) on a forearm (110) of a human patient is illustrated. In accordance with the particular kind of medical or cosmetic application desired, the end region of the tube (50) can be located in contact or in proximity of the body region of interest.

Figure 6:
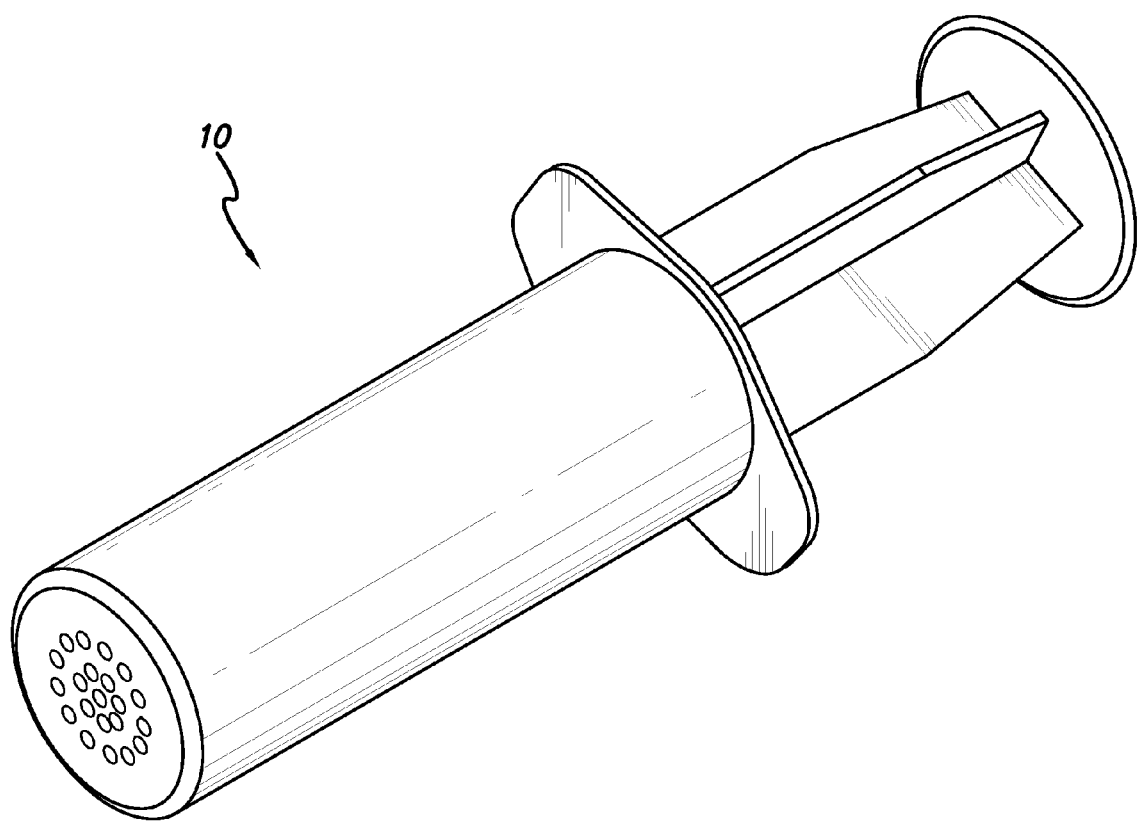
FIG. 6 shows a perspective view of an embodiment of the dispenser without closing cap.

FIG. 6 shows a perspective view of an embodiment of the dispenser (10) without closing cap.

Figure 7:
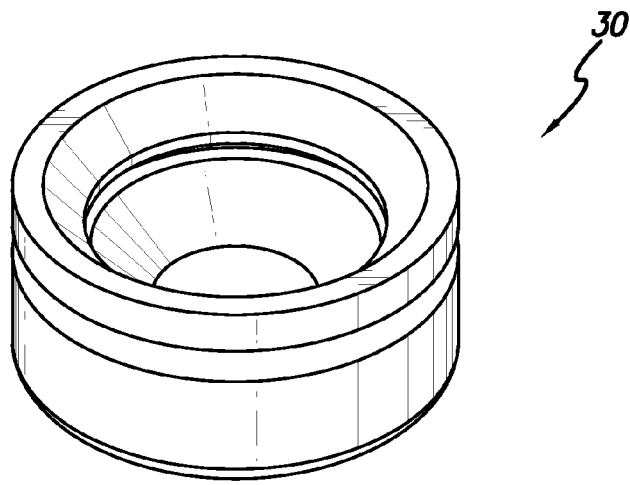
FIG. 7 is a perspective view showing in detail a plunger ring located at the bottom of the plunger of the dispenser.

FIG. 7 is a perspective view showing in detail the plunger ring (30) located at the bottom of the plunger (20) of the dispenser (10), as already shown in FIG. 1.

Figure 4:
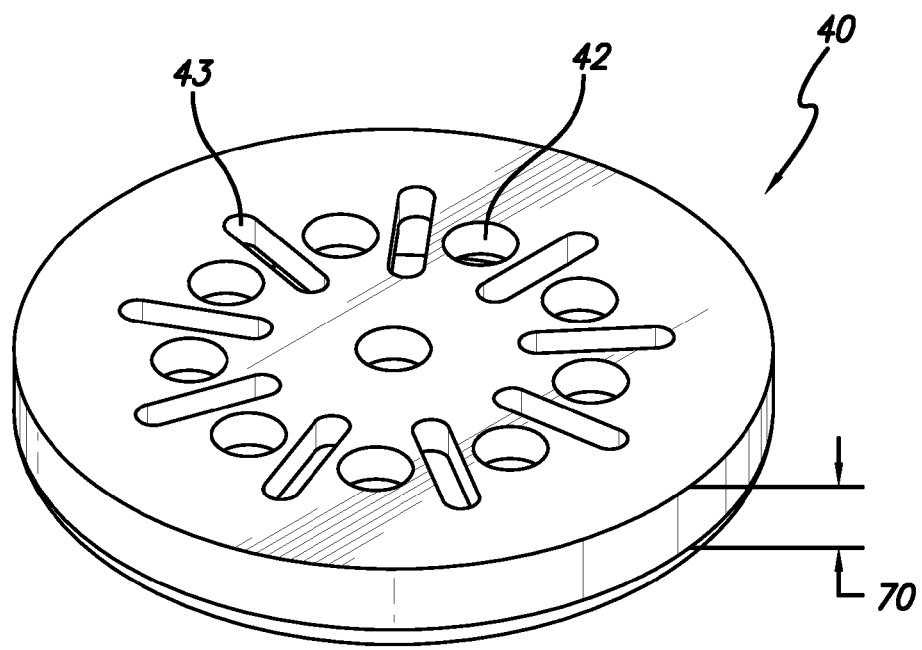
FIGS. 4 and 5 are a top perspective view and a bottom perspective view, respectively, of the perforated element shown in FIG. 1.
Figure 5:
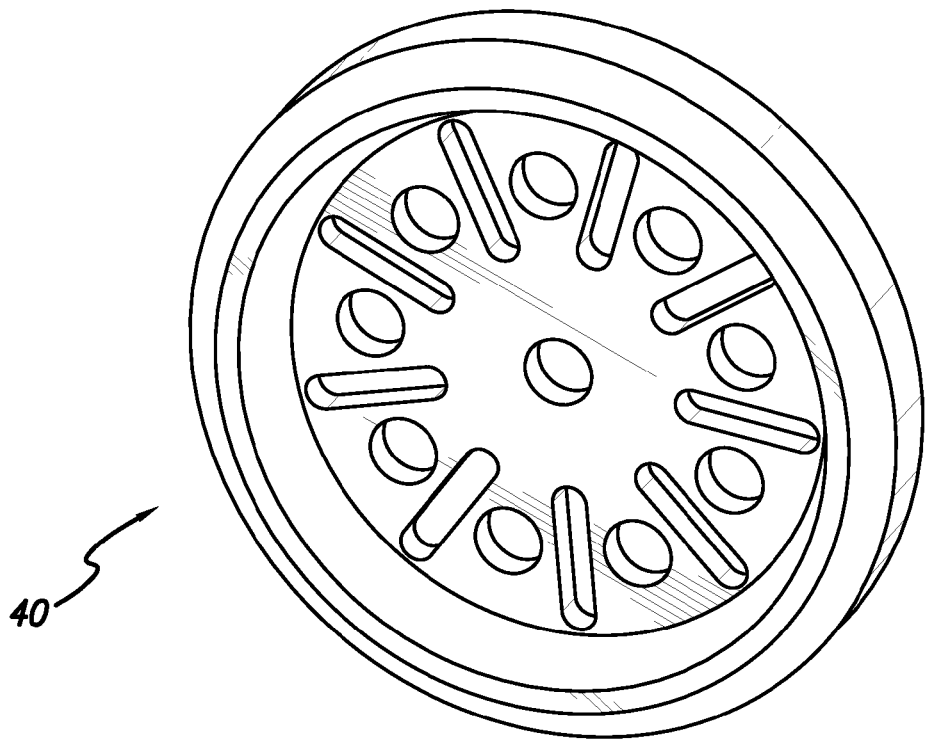

As mentioned above, FIGS. 4 and 5 are a top perspective view and a bottom perspective view, respectively, of the perforated element (40) shown in FIG. 1. In the exemplary embodiment of those figures, the perforated element (40) comprises a pattern of holes (42) and slits (43), or more generally perforations, that allow passage of the substance from the interior of the tube (50) to the skin of the patient through the perforated bottom (57) of the tube (50). It should be noted that a distance from the top surface of the perforated element and the bottom of the tube (50) can be controlled by controlling the height (70) of the perforated element (40), as shown in FIG. 4. In particular, different values of the height (70) will allow different timings and/or release pressures of the substance on the skin of the patient. By way of example, it may be desirable to avoid that the substance spreads quickly over the skin of the patient. Such effect can be prevented by providing a selected value of the height (70). The higher the height the lower the spreading velocity of the substance and vice versa.

Figure 8:
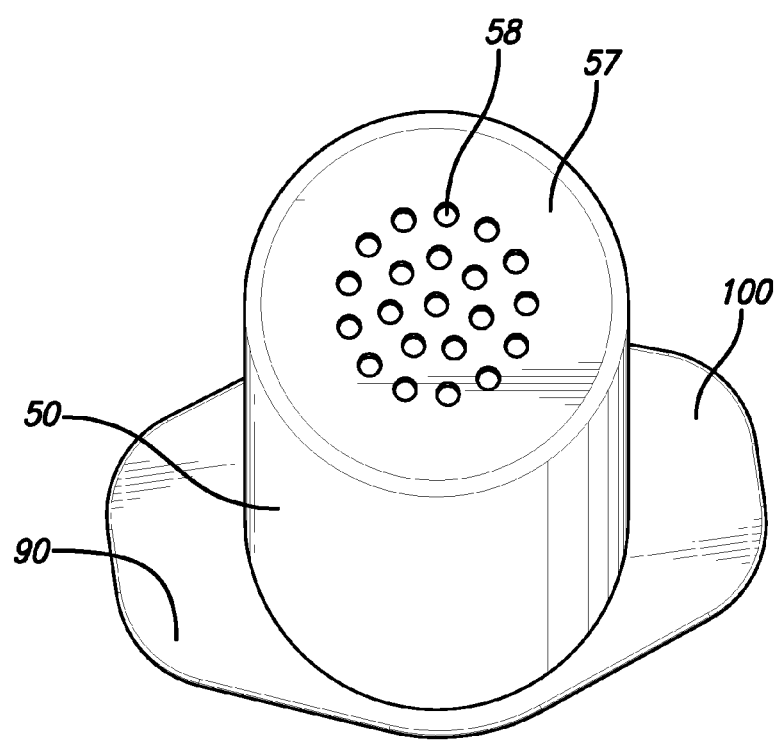
FIG. 8 shows a bottom perspective view of the tube of the dispenser.

FIG. 8 shows a bottom perspective view of the tube (50) of the dispenser, where an embodiment of the perforated bottom (57) is shown in detail. Also shown in FIG. 7 are two wings (90, 100) (see also FIGS. 1, 2 and 6) which allow lodging of the fingers of the operator while pushing the dispenser's plunger in the tube (50). In particular, wings (90, 100) provide a better comfort to the operator and allow a better handling of the dispenser during use, when the dispenser is located near or over some part of the human or animal body.

It should be noted that according to several embodiments of the present disclosure, the shape of the bottom (57) and the perforated element (40) is round. Such kind of shape allows several useful applications: i) the dispenser (10) can easily slide on different parts of the human or animal body when in use; ii) the substance inside the dispenser (liquid, gel, glue etc) can be better controlled because of the snug coupling between the perforated element (40) and the interior surface of the tube (50), which prevents the substance from spreading away through any irregular edges of the perforated element (40) or any space left between the perforated element (40) and the interior of the tube (50). A better control of the substance allows the operator to better maneuver the dispenser (10) on the body of the patient, with improved results.

The person skilled in the art will also understand that the shape and number of holes or openings in the perforated element (40) and the height of the perforated element (40) can vary according to the circumstances and the various applications or filtering uses of the perforated element (40) according to the various circumstances.

More generally, speed control of the substance is subject to three variables, one of them being an outer variable provided by the viscosity and density of the substance (which generally cannot be controlled) and two internal variables which instead can be controlled: i) the geometry of the perforated element (40) (inclusive of shape, size, amount and size of holes) and ii) the geometry of the bottom opening (57) (inclusive of shape, size, amount and size of holes).

Additionally, the location of the holes or openings in the perforated element (40) can be changed so that these holes or openings vertically correspond or do not correspond to the holes and/or openings of the perforated bottom (57). Presence of such alignment will reduce the path of the substance from the dispenser to the skin of the patient, thus resulting in a faster application. On the other hand, absence of such alignment will increase the path of the substance from the dispenser to the skin of the patient, thus resulting in a slower application.

It should also be noted that an optimized choice of the above parameters will also allow a more rationed use of the substance. A rationed use of the substance can imply a reduced cost to the operator in terms of the amount of substance to be bought.

It should also be noted that the dispenser according to the present disclosure can be disposable (if, for example, used in a medical facility where several patients are treated) or non-disposable (if, for example, the dispenser is for personal use). Additionally, the size of the dispenser can be varied according to the various applications. For example, applications on some parts of the body (e.g., chest) may require a larger size, if desired.

As mentioned above, cap (60) closes the perforated bottom (57) of the tube (50) when the dispenser (10) is not in use. This allows isolation of the substance from any outside environment. It should also be noted that the presence of the cap (60) further allows the dispenser (10) to be closed also during a procedure performed by a doctor or operator, in case such procedure contains steps which are additional to the application of the substance on the patient. By way of example, when a doctor performs a laser application on the patient (or other applications such as tomography applications) after application of the substance, there is no need to keep the dispenser open, and such dispenser can be closed by the cap during such laser application. This is especially useful if the procedure involves several substance application steps followed by, e.g., laser therapy. During all these therapy steps (e.g., light pulse therapy or tomography) the dispenser (10) can be conveniently closed by the cap (60), thus minimizing any exposure of the substance to the outside environment.

A further use of the cap (60) is that of allowing the operator to spread the substance over the body of the patient once the substance has been applied by using the dispenser (10) covered by such cap (60).

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. Unless defined otherwise, all technical and scientific terms used herein have the same meaning as commonly understood by one of ordinary skill in the art to which the disclosure pertains.

The examples set forth above are provided to give those of ordinary skill in the art a complete disclosure and description of how to make and use the embodiments of the reference processing methods of the disclosure, and are not intended to limit the scope of what the inventors regard as their disclosure. Modifications of the above-described modes for carrying out the disclosure may be used by persons of skill in the video art, and are intended to be within the scope of the following claims.

A number of embodiments of the disclosure have been described. Nevertheless, it will be understood that various modifications may be made without departing from the spirit and scope of the present disclosure. Accordingly, other embodiments are within the scope of the following claims.

The invention claimed is:

1. A dispenser adapted to contain a substance to be applied on a human or animal patient, comprising:
a plunger;

a tube, the plunger being adapted to slide inside the tube for application of the substance, the tube containing a plurality of openings at a first end region thereof, the first end region of the tube having a planar face, the plurality of openings being located on the planar face of the first end region, the planar face of the first end region being adapted to spread the substance on a skin region of the human or animal patient during application of the substance to the skin region;

a perforated element located inside the tube, the perforated element having a height that provides a distance between perforations of the perforated element and the first end region, wherein location of the perforated element inside the tube is such that the substance to be applied is adapted to be disposed inside the tube above the perforated element before application, and wherein, during use of the dispenser, the plunger slides inside the tube to push the substance through the perforated element and through the plurality of openings at the first end region of the tube, thus expelling the substance from the dispenser for application on the human or animal patient, the height further defining a maximum length of run of the plunger inside the tube during use of the dispenser; wherein correspondence or lack of correspondence between perforations of the perforated element and the plurality of openings on the planar face is selectable to obtain a desired path length and a consequent desired application delay of the substance on the skin of the human or animal patient.

2. The dispenser of claim 1, wherein geometry of the perforated element is selectable to obtain a desired path length and a consequent desired application delay of the substance on the human or animal patient.

3. The dispenser of claim 2, wherein said geometry of the perforated element is selected from the height of the perforated element and/or shape, size and/or amount of perforations.

4. The dispenser of claim 1, further comprising a cap to cover the end region of the tube.

5. A method of using the dispenser of claim 4, comprising: sliding the dispenser over a substance-covered body part of the patient to spread the substance.

6. The dispenser of claim 1, wherein the tube comprises side wings at a second end region thereof opposite the first end region.

7. The dispenser of claim 6, wherein the perforated element comprises a plurality of holes and/or slits.

8. The dispenser of claim 1, further comprising the substance, prefilled in the tube.

9. The dispenser of claim 8, wherein the substance is prefilled after fabrication of the dispenser.

10. The dispenser of claim 1, said dispenser being a disposable dispenser.

11. The dispenser of claim 1, wherein the perforated element is located at a bottom of the tube, in proximity of said first end region.

12. A method of using the dispenser of claim 1, comprising:
locating the end region of the tube in proximity of or on a body region of the human or animal patient;
pushing the plunger inside the tube, whereby the substance passes through the perforated element and through the plurality of openings and is expelled from the tube and applied to the skin region of the human or animal patient.

13. The method of claim 12, further comprising moving the dispenser along the skin region while pushing the plunger inside the tube.

14. The dispenser of claim 1, wherein a perimeter of the planar face is round.

* * * * *